United States Patent
Wang

(10) Patent No.: US 11,026,907 B2
(45) Date of Patent: Jun. 8, 2021

(54) AZELAIC ACID GEL, PREPARATION METHOD AND APPLICATION THEREOF

(71) Applicant: CHENGDU JOY YOUNG BIOTECHNOLOGY CO., LTD., Sichuan (CN)

(72) Inventor: Guangji Wang, Sichuan (CN)

(73) Assignee: CHENGDU JOY YOUNG BIOTECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 16/960,025

(22) PCT Filed: Jun. 26, 2019

(86) PCT No.: PCT/CN2019/093004
§ 371 (c)(1),
(2) Date: Jul. 3, 2020

(87) PCT Pub. No.: WO2020/019927
PCT Pub. Date: Jan. 30, 2020

(65) Prior Publication Data
US 2020/0345672 A1    Nov. 5, 2020

(30) Foreign Application Priority Data

Jul. 25, 2018 (CN) .......................... 201810825807.7

(51) Int. Cl.
| | | |
|---|---|---|
| *A61K 31/194* | (2006.01) | |
| *A61P 17/10* | (2006.01) | |
| *A61K 9/00* | (2006.01) | |
| *A61K 9/06* | (2006.01) | |
| *A61K 31/60* | (2006.01) | |
| *A61K 47/32* | (2006.01) | |

(52) U.S. Cl.
CPC .......... *A61K 31/194* (2013.01); *A61K 9/0014* (2013.01); *A61K 9/06* (2013.01); *A61K 31/60* (2013.01); *A61K 47/32* (2013.01); *A61P 17/10* (2018.01)

(58) Field of Classification Search
None
See application file for complete search history.

(56) References Cited

FOREIGN PATENT DOCUMENTS

| | | |
|---|---|---|
| CN | 1130875 | 9/1996 |
| CN | 102764256 | 11/2012 |
| CN | 105708718 A * | 6/2016 |
| CN | 107257688 | 10/2017 |
| CN | 108553411 | 9/2018 |
| CN | 106420787 | 5/2020 |
| WO | 2012177433 | 12/2012 |

OTHER PUBLICATIONS

"International Search Report (Form PCT/ISA/210)" of PCT/CN2019/093004, dated Sep. 26, 2019, with English translation thereof, pp. 1-4.

* cited by examiner

*Primary Examiner* — Nannette Holloman
(74) *Attorney, Agent, or Firm* — JCIP Global Inc.

(57) ABSTRACT

An azelaic acid gel, and a preparation method and an application thereof. The azelaic acid gel comprises the following components in percentage by weight: azelaic acid: 10-20%; salicylic acid: 0.5-2%; a polyacrylate cross-linked polymer-6: 1-3%; 1,3-propylene glycol: 60-74%; and the remaining part being water. The azelaic acid gel is used for preparing medicines for preventing or treating acnes.

11 Claims, No Drawings

AZELAIC ACID GEL, PREPARATION METHOD AND APPLICATION THEREOF

CROSS-REFERENCE TO RELATED APPLICATION

This application is a 371 of international application of PCT application serial no. PCT/CN2019/093004, filed on Jun. 26, 2019, which claims the priority benefit of China application no. 201810825807.7, filed on Jul. 25, 2018. The entirety of each of the above mentioned patent applications is hereby incorporated by reference herein and made a part of this specification.

BACKGROUND

Technical Field

The invention relates to an azelaic acid gel, preparation method and application thereof, and belongs to the technical field of skin drugs.

Description of Related Art

Acnes is a chronic inflammatory skin disease of the pilosebaceous unit that is commonly seen in adolescents. Such a disease exerts a great psychological and social impact on the adolescents, but often lightens or gets well naturally after adolescence. From the perspective of clinical manifestations, acnes are characterized by pleomorphic skin lesions such as comedones, papules, pustules, nodules and the like, which are prone to occur on the face.

According to a joint survey carried out by Chinese Association of Dermatology and Chinese Youth Federation, the incidence rate of acnes is on the rise year by year in China and more than 80% of the population has been plagued with acne problems to varying degrees. At least one in three young people are suffering from severe acnes, including 294 million middle school students, 133 million college students, and 127 million white-collar workers over 25 years old, amounting to 550 million people.

According to incomplete statistics, Chinese anti-acne consumers are increasing by 4-6 million persons-times per year, and China is seeing a fast growing anti-acne market like never before. Based on the annual average anti-acne cost of 500 yuan each person willing to be treated, the anti-acne market scale has reached 70 billion yuan.

The mild and moderate acne patients would prefer not to treat or take acne products on the market, while severe acne patients are willing to get treatment in hospitals and acne institutions. However, the anti-acne institutions and products on the market cannot completely eliminate acnes and have side effects. Hospitals are not concentrated on and beauty salons are not specialized in this aspect. According to the authoritative statistics of Ministry of Health of the People's Republic of China, the complete cure rate of acnes is only 32.95% in China. Therefore, there is an urgent need for a drug that can improve the cure rate of acnes.

Azelaic acid, also known as anchoic acid, is white to yellowish monoclinic prism, acicular crystal or powder in appearance. Due to the antibacterial effect, it can directly inhibit and kill bacteria on skin surface and in hair follicle, competitively inhibit the process of producing dihydrotestosterone and reduce excessive skin oil induced by dihydrotestosterone, inhibit the production and action of reactive oxygen radicals, and thus is conducive to anti-inflammation. It is often used for the treatment of acnes, acne rosacea and pigmentation disorder, and can increase the absorption function of skin due to good permeability to the skin. However, it is thermolabile and should not be added at high temperature. It is soluble in hot water, alcohol and some polyols, slightly soluble in cold water, ether and benzene.

At present, azelaic acid is often made into ointments. For example, the patent for invention with the application number of 201610786026.2 discloses an acne cream and preparation method thereof. The acne cream consists of a morning ointment and a night ointment, the night ointment comprises a second raw material and a cream matrix, and the second raw material consists of the following substances: 10% of azelaic acid, 0.1% of adapalene, 1% of clindamycin, 1% of salicylic acid, 1.5% of fatty azone and 0.2% of nepal methyl ester. For another example, the patent for invention with the application number of 201210230433.7 discloses an ointment for treating acnes, which are prepared by mixing 3% of oxymatrine, 1% of vitamin E, 2% of azelaic acid, 0.5% of menthol, 5% of 2901, 3% of boric acid, 2% of azone and 83.5% of cream matrix by mass.

In the patents above, azelaic acid is made into ointments without exception. Now, the azelaic acid products available in the market are often made into ointments to increase their solubility and permeability. Oily raw materials can help dissolve azelaic acid and auxiliary penetrant (usually oily raw materials) and make it well permeable to the skin. Thus, the product can only be oily cream or emulsion. The amount of azelaic acid is proportional to that of oily raw materials. As a result, the amount of auxiliary penetrant and the side effects will increase correspondingly. So, the cream type of azelaic acid has heavy oil feeling, poor air permeability, large side effects and low content of effective substances.

SUMMARY

In view of the above defects, the disclosure provides a new azelaic acid dosage form; that is, azelaic acid gel. Compared with creams, the gel doesn't contain any oily components and has good efficacy on acne prevention or treatment.

The azelaic acid gel comprises the following components by weight percentage: 10-20% of azelaic acid, 0.5-2% of salicylic acid, 1-3% of ZEN, 60-74% of 1,3-propylene glycol and the remaining part being water.

Preferably, the azelaic acid gel comprises the following components by weight percentage: 12-18% of azelaic acid, 0.8-1.5% of salicylic acid, 1.5-2.5% of ZEN, 65-72% of 1,3-propylene glycol and the remaining part being water.

Preferably, the azelaic acid gel comprises the following components by weight percentage: 15% of azelaic acid, 2% of ZEN, 1% of salicylic acid, 70% of 1,3-propylene glycol and 12% of water.

Preferably, the water is deionized water.

The disclosure also provides a method for preparing the azelaic acid gel.

The method for preparing the azelaic acid gel comprises the following steps:

a. uniformly dispersing ZEN in 1,3-propylene glycol and then uniformly mixing with water to obtain solution A;

b. uniformly dispersing azelaic acid in 1,3-propylene glycol and heating to 65-80° C. to obtain solution B;

c. uniformly dispersing salicylic acid in 1,3-propylene glycol to obtain solution C; and d. mixing solution A, solution B and solution C, stirring at 55-65° C., and cooling to room temperature to obtain an azelaic acid gel.
}

There is no time sequence between step a, step b and step c, which can be performed in an arbitrary order or simultaneously. Solution A, solution B and solution C should be mixed and stirred finally.

The disclosure also provides applications of the azelaic acid gel in preparing drugs for preventing or treating acnes.

The azelaic acid gel can be used for the treatment or prevention of acnes, so as to improve the cure rate of acne patients, reduce facial skin damage to patients due to acnes, alleviate their physiological and psychological pain, and reduce the treatment cost and medical expenses.

Compared with the prior art, the disclosure has the following beneficial effects:

In the disclosure, azelaic acid is prepared into a gel by combining specific raw materials, which is transparent, free from any precipitation and well permeable to human skin. The product can be used for the treatment or prevention of acnes, and improve the cure rate of acne patients.

The azelaic acid gel is based on an oil-free formula (compared with creams). It will not increase the burden on skin or clog pores after applied to oily skin, thereby eliminating the hidden danger of acnes. Compared with the ointment-like azelaic acid, the gel-like azelaic acid is simply and easily permeable to acne skin and saves additional grease required for aiding dissolution and permeability, which avoids corresponding side effects caused by excessive introduction of oily substances. Smooth hair follicle tubes will facilitate the excretion of grease and other metabolites in the later stage of anti-acne process. Due to the anti-inflammatory and sterilizing effect, the azelaic acid can help unblock the hair follicles, smoothly solve the excretion problem and reduce the possibility of recurrence of acnes.

Free of any preservatives, the azelaic acid gel has simple components, which provide the antibacterial effect and the features of simple preparation method and low cost.

DESCRIPTION OF THE EMBODIMENTS

The azelaic acid gel of the disclosure comprises the following components by weight percentage: 10-20% of azelaic acid, 0.5-2% of salicylic acid, 1-3% of ZEN, 60-74% of 1,3-propylene glycol and the remaining part being water.

Among them, ZEN is polyacrylate cross-linked polymer-6, produced by SEPPIC under the trade name SepiMAX ZEN. Electrolyte generated through electrolysis of azelaic acid can destroy the structure of carbomer, while ZEN is an associative polymer with excellent electrolytic resistance, can resist the damage of electrolyte to the formula to the greatest extent, and produce transparent hydrogel products with moist and elegant touch and velvet texture depending on its good suspension stability. Researches reveal that the azelaic acid gel can be successfully prepared by ZEN only. If the amount of ZEN added is too low, the obtained product is thin and flowable, and cannot be prepared into a gel. Otherwise, the product is too dry to be used.

We found that the azelaic acid doesn't affect the structure of ZEN. If only water was used as the solvent, the transparency of the product was too low, and azelaic acid crystals would precipitate at the room temperature; anhydrous ethanol or 1,3-propylene glycol could change the precipitation of azelaic acid. However, anhydrous ethanol could not change the transparency of the product, and 1,3-propylene glycol could not only solve the problem of azelaic acid precipitation, but also change the transparency of the product to obtain a transparent gel without alcohol taste. Thus, a certain amount of 1,3-propylene glycol and water are mixed as a solvent in the disclosure to obtain a transparent gel product that is moderately consistent, not flowable, and free from crystallization and alcohol smell.

Salicylic acid can soften and exfoliate cutin, reduce the clogged follicles. Thus, it has good effect on adolescent comedones and common acnes. According to research, the amount of salicylic acid in the disclosure is preferably 0.5-2%. A specific amount of salicylic acid is mixed with azelaic acid to play a synergistic effect and improve the treatment effect on acnes.

Preferably, the azelaic acid gel comprises the following components by weight percentage: 12-18% of azelaic acid, 0.8-1.5% of salicylic acid, 1.5-2.5% of ZEN, 65-72% of 1,3-propylene glycol and the remaining part being water.

In a preferred embodiment of the disclosure, the azelaic acid gel comprises the following components by weight percentage: 15% of azelaic acid, 2% of ZEN, 1% of salicylic acid, 70% of 1,3-propylene glycol and 12% of water.

Preferably, the water is deionized water.

The second solution in the invention is to provide a method for preparing the azelaic acid gel.

The method for preparing azelaic acid gel according to the invention comprises the following steps:

a. uniformly dispersing ZEN in 1,3-propylene glycol and then uniformly mixing with water to obtain solution A;

b. uniformly dispersing azelaic acid in 1,3-propylene glycol and heating to 65-80° C. to obtain solution B;

c. uniformly dispersing salicylic acid in 1,3-propylene glycol to obtain solution C; and d. mixing solution A, solution B and solution C, stirring at 55-65° C., and cooling to room temperature to obtain an azelaic acid gel.

Among them, there is no time sequence between step a, step b and step c, which can be performed in an arbitrary order or simultaneously. Solution A, solution B and solution C should be mixed and stirred finally.

The disclosure also provides applications of the azelaic acid gel in preparing drugs for preventing or treating acnes.

The azelaic acid gel of the disclosure can be used for the treatment or prevention of acnes, so as to improve the cure rate of acne patients, reduce facial skin damage to patients due to acnes, alleviate their physiological and psychological pain, and reduce the treatment cost and medical expenses.

The specific embodiments of the invention will be described in detail in combination with the examples, and the invention is not limited to the scope of the described examples. The raw materials used in the examples include:

ZEN, purchased from SEPPIC;

azelaic acid, purchased from Shanghai Linen Technology Development Co., Ltd.;

salicylic acid, purchased from Shandong Xinhua Pharmaceutical Co., Ltd.;

1,3-propylene glycol of corn source, purchased from DuPont Engineering Polymers;

water: self-produced deionized water.

Example 1

The azelaic acid gel was prepared according to the following steps:

a. uniformly dispersing ZEN in 1,3-propylene glycol and then uniformly mixing with water to obtain solution A;

b. uniformly dispersing azelaic acid in 1,3-propylene glycol and heating to 75° C. to obtain solution B;

c. uniformly dispersing salicylic acid in 1,3-propylene glycol to obtain solution C; and d. mixing solution A, solution B and solution C, stirring at 60° C., and cooling to room temperature to obtain an azelaic acid gel.

The formula of each raw material is shown in Table 1.

TABLE 1

| Solution | Raw materials | Added amount (Wt. %) |
|---|---|---|
| A | 1,3-propylene glycol | 45.00 |
|  | Azelaic acid | 15.00 |
| B | Water | 12.00 |
|  | 1,3-propylene glycol | 20.00 |
|  | ZEN | 2.00 |
| C | Salicylic acid | 1.00 |
|  | 1,3-propylene glycol | 5.00 |

Based on the formula, a certain amount of bacteria (18000 cfu/g or mold 8700 cfu/g liquid) was artificially introduced, from which a quantitative sample was taken to determine the bacteriostatic effect. The results are shown in Table 2.

TABLE 2

| Time | Microbiological test results | |
|---|---|---|
| Day 3 | Total bacterial count (CFU/g) | <10 |
|  | Total count of mold and yeast (CFU/g) | <10 |
| Day 7 | Total bacterial count (CFU/g) | <10 |
|  | Total count of mold and yeast (CFU/g) | <10 |
| Day 15 | Total bacterial count (CFU/g) | <10 |
|  | Total count of mold and yeast (CFU/g) | <10 |
| Day 21 | Total bacterial count (CFU/g) | <10 |
|  | Total count of mold and yeast (CFU/g) | <10 |

It can be seen from Table 2 that the system still has the antibacterial effect although no preservatives are added to it.

Examples 2-4

The azelaic acid gel was prepared according to the method described in Example 1. The total amount of each raw material is shown in Table 3.

TABLE 3

| | Added amount of raw materials (Wt. %) | | | | |
|---|---|---|---|---|---|
| Example No. | Azelaic acid | Salicylic acid | ZEN | 1,3-propylene glycol | Water |
| Example 2 | 12 | 1.5 | 1.5 | 65 | 20 |
| Example 3 | 18 | 0.8 | 2.5 | 72 | 6.7 |
| Example 4 | 14 | 1.2 | 2.1 | 70 | 12.7 |

The products of Examples 2 to 4 were also tested to have antibacterial properties.

REFERENCE 1

Based on the actual formula experience of developing gel products in the past, the matrix formula components of azelaic acid gel were designed as follows: CP-940 (Shanghai Yanglong Industry Co., Ltd.), azelaic acid (Shanghai Linen Technology Development Co., Ltd.), sodium hydroxide (analytically pure AR, Chengdu Kelon Chemical Reagent Factory), and water (self-produced deionized water).

CP-940 is a high molecular polymer and its aqueous solution is acidic. It can slowly swell in water and its curled molecules will expand due to electric repulsion, thus achieving the thickening effect. Sodium hydroxide and triethanolamine are commonly used as neutralizing agents. In consideration of the acidic characteristics of azelaic acid, the proportion of CP-940 was increased on the basis of previous gel formula. The addition amounts of CP-940 were 0.5%, 1.0%, 1.5% and 2.0% respectively; on this basis, we added 15% of azelaic acid. The results are shown in Table 4.

TABLE 4

| Raw materials | Sample No. | | | | | | | |
|---|---|---|---|---|---|---|---|---|
| | 1# | 2# | 3# | 4# | 5# | 6# | 7# | 8# |
| | Added amount (Wt. %) | | | | | | | |
| CP-940 | 0.5 | 1.0 | 1.5 | 2.0 | 0.5 | 1.0 | 1.5 | 2.0 |
| NaOH | 0.135 | 0.27 | 0.405 | 0.54 | 0.135 | 0.27 | 0.405 | 0.54 |
| Azelaic acid | 0 | | | | 15 | | | |
| Water | To 100 | | | | | | | |
| Appearance | Transparent condensation | Transparent condensation | Transparent gel | Transparent gel | Translucent liquid | Translucent liquid | Translucent liquid | Translucent liquid |
| Consistency | Relatively thick, basically stagnant | Thick and stagnant | Very thick and stagnant | Very thick and stagnant | Very thin and flowable | Very thin and flowable | Very thin and flowable | Very thin and flowable |

It can be seen that azelaic acid can affect the structure of CP-940 greatly although it is slightly soluble in cold water.

Considering the electrolyte properties of azelaic acid, we decided to prepare the basic gel again rather than neutralize CP-940 with alkali. The results are shown in Table 5.

TABLE 5

| Raw materials | Sample No. | | | | | | | |
|---|---|---|---|---|---|---|---|---|
| | 1# | 2# | 3# | 4# | 5# | 6# | 7# | 8# |
| | Added amount (Wt. %) | | | | | | | |
| CP-940 | 0.5 | 1.0 | 1.5 | 2.0 | 0.5 | 1.0 | 1.5 | 2.0 |
| Azelaic acid | 0 | | | | 15 | | | |
| Water | To 100 | | | | | | | |
| Appearance | Transparent condensation | Transparent condensation | Transparent gel | Transparent gel | Translucent liquid | Translucent liquid | Translucent liquid | Translucent liquid |
| Consistency | Relatively thin and flowable | Slightly thin and flowable | Slightly thin and flowable | Slightly thick and stagnant | Very thin and flowable | Very thin and flowable | Very thin and flowable | Very thin and flowable |

It can be seen that azelaic acid will destroy the structure of CP-940 regardless of whether CP-940 is neutralized or not. Therefore, it is not feasible to use CP-940 as the matrix component of gel.

Example 5 Acne Treatment Test

The efficacy on acne was determined by combining the products of Examples 1 to 4, and taking the azelaic acid cream (formula of azelaic acid cream: 15% of azelaic acid, 1% of salicylic acid and 84% of cream matrix) as a reference. The specific experimental method is as follows:

The acne patients aged 14-40 years old, regardless of gender, were tested according to Pillsbury grades 1-4.

The acne classification criteria (improved Pillsbury grading method) were as follows: Grade 0: very small comedones or papules (not included in the subject criteria); Grade I (mild): scattered papules and comedones with pustules and lesions ranging from 10 to 25; Grade II (moderate): piles of papules and comedones with pustules and lesions ranging from 25 to 50; Grade III (severe): papules, comedones and pustules with more than 50 lesions and nodules less than 5; Grade IV (extremely severe): piles of severe papules and comedones with pustules, nodules, cysts and scars.

Exclusion criteria: acne patients treated by local administration within 2 weeks; acne patients treated systematically with antibiotics or other drugs within 4 weeks; those with open wound or decayed face on the affected part of acnes; those with other diseases having received drug therapy that may affect acnes; pregnant or lactating women; patients suffering from other skin diseases that may affect the efficacy, such as psoriasis, lupus erythematosus and hormone-dependent dermatitis; and those known allergy to azelaic acid.

Administration method: apply a thin layer of medicine to the acne area of the face once in the morning and once in the evening, and avoid the eyes and mucous membrane. No other external drugs and antibiotics were used during the test. The treatment course was 6 weeks, and follow-up visits were made once every 2 weeks.

Indicator for observation: The curative effect indicator and adverse reactions were observed and recorded during the first visit after treatment and the follow-up visit in second, fourth and sixth week. The curative effect indicator includes inflammatory damage (inflammatory papules and pustules) and non-inflammatory damage (whitehead and blackhead). Inflammatory lesion count: Facial papules, pustules, nodules and cysts were counted separately before treatment and the follow-up visit in second, fourth and sixth week; non-inflammatory lesion count: The facial whitehead and blackhead were counted separately before treatment and during the follow-up visit separately in second, fourth and sixth week;

Laboratory examination: Blood and urine routine were examined before and after treatment respectively, of which 12 cases were examined for liver function (TI, ALT) and renal function (BUN, Cr).

Efficacy criteria: The main efficacy is reflected in the reduction of total inflammatory lesions (sum of papules and pustules), and the total efficacy was evaluated in week 6.

The criteria are as follows:

Recovery: damage reduction ≥90%;

Obvious effect: damage reduction of 60%-89%;

Improvement: damage reduction of 20%-59%;

Ineffectiveness: No change in disease condition or reduced damage results.

Each product involved 30 patients to observe their curative effects and adverse reactions. The results are shown in Table 6.

TABLE 6

| Product No. | Treatment cycle | Recovery | Obvious effect | Improvement | Ineffectiveness | Marked effective rate |
|---|---|---|---|---|---|---|
| Example 1 Product | 2 weeks | 6 | 10 | 6 | 8 | 53.33% |
| | 4 weeks | 10 | 8 | 8 | 4 | 60.00% |
| | 6 weeks | 12 | 13 | 3 | 2 | 83.33% |
| Example 2 Product | 2 weeks | 5 | 9 | 9 | 7 | 46.67% |
| | 4 weeks | 9 | 7 | 9 | 5 | 53.33% |
| | 6 weeks | 12 | 11 | 5 | 2 | 76.67% |
| Example 3 Product | 2 weeks | 6 | 9 | 8 | 7 | 50.00% |
| | 4 weeks | 9 | 9 | 8 | 4 | 60.00% |
| | 6 weeks | 12 | 12 | 5 | 1 | 80.00% |
| Example 4 Product | 2 weeks | 5 | 10 | 7 | 8 | 50.00% |
| | 4 weeks | 9 | 8 | 8 | 5 | 56.67% |
| | 6 weeks | 11 | 12 | 4 | 3 | 76.67% |
| Reference 1 Product | 2 weeks | 3 | 8 | 12 | 7 | 36.67% |
| | 4 weeks | 7 | 6 | 12 | 5 | 43.33% |
| | 6 weeks | 8 | 9 | 9 | 4 | 56.67% |

Adverse reaction: For patients applying the product of the disclosure, the adverse reactions are mainly burning pain, pruritus, erythema, edema, dryness and desquamation, all of which were relatively mild, and most of which were untreated and did not affect the treatment effect.

What is claimed is:

1. An azelaic acid gel for preventing or treating acnes, comprising the following components by weight percentage: 10-20% of azelaic acid, 0.5-2% of salicylic acid, 1-3% of polyacrylate cross-linked polymer-6, 60-74% of 1,3-propylene glycol, and the remaining part being water.

2. The azelaic acid gel for preventing or treating acnes according to claim 1, wherein the azelaic acid gel comprises the following components by weight percentage: 12-18% of azelaic acid, 0.8-1.5% of salicylic acid, 1.5-2.5% of polyacrylate cross-linked polymer-6, 65-72% of 1,3-propylene glycol, and the remaining part being water.

3. The azelaic acid gel for preventing or treating acnes according to claim 1, wherein the azelaic acid gel comprises the following components by weight percentage: 15% of azelaic acid, 2% of polyacrylate cross-linked polymer-6, 1% of salicylic acid, 70% of 1,3-propylene glycol, and 12% of water.

4. The azelaic acid gel for preventing or treating acnes according to claim 1, wherein the water is deionized water.

5. A method for preparing the azelaic acid gel for preventing or treating acnes according to claim 1, comprising the following steps:
   a. uniformly dispersing polyacrylate cross-linked polymer-6 in 1,3-propylene glycol and then uniformly mixing with water to obtain solution A;
   b. uniformly dispersing azelaic acid in 1,3-propylene glycol and heating to 65-80° C. to obtain solution B;
   c. uniformly dispersing salicylic acid in 1,3-propylene glycol to obtain solution C; and
   d. mixing solution A, solution B and solution C, stirring at 55-65° C., and cooling to room temperature to obtain an azelaic acid gel.

6. A method, comprising: preparing a drug comprising the azelaic acid gel according to claim 1; and using the drug to treat or prevent acnes.

7. The azelaic acid gel for preventing or treating acnes according to claim 2, wherein the water is deionized water.

8. The azelaic acid gel for preventing or treating acnes according to claim 3, wherein the water is deionized water.

9. A method for preparing the azelaic acid gel for preventing or treating acnes according to claim 2, comprising the following steps:
   a. uniformly dispersing polyacrylate cross-linked polymer-6 in 1,3-propylene glycol and then uniformly mixing with water to obtain solution A;
   b. uniformly dispersing azelaic acid in 1,3-propylene glycol and heating to 65-80° C. to obtain solution B;
   c. uniformly dispersing salicylic acid in 1,3-propylene glycol to obtain solution C; and
   d. mixing solution A, solution B and solution C, stirring at 55-65° C., and cooling to room temperature to obtain an azelaic acid gel.

10. A method for preparing the azelaic acid gel for preventing or treating acnes according to claim 3, comprising the following steps:
    a. uniformly dispersing polyacrylate cross-linked polymer-6 in 1,3-propylene glycol and then uniformly mixing with water to obtain solution A;
    b. uniformly dispersing azelaic acid in 1,3-propylene glycol and heating to 65-80° C. to obtain solution B;
    c. uniformly dispersing salicylic acid in 1,3-propylene glycol to obtain solution C; and
    d. mixing solution A, solution B and solution C, stirring at 55-65° C., and cooling to room temperature to obtain an azelaic acid gel.

11. A method for preparing the azelaic acid gel for preventing or treating acnes according to claim 4, comprising the following steps:
    a. uniformly dispersing polyacrylate cross-linked polymer-6 in 1,3-propylene glycol and then uniformly mixing with water to obtain solution A;
    b. uniformly dispersing azelaic acid in 1,3-propylene glycol and heating to 65-80° C. to obtain solution B;
    c. uniformly dispersing salicylic acid in 1,3-propylene glycol to obtain solution C; and
    d. mixing solution A, solution B and solution C, stirring at 55-65° C., and cooling to room temperature to obtain an azelaic acid gel.

* * * * *